United States Patent [19]
Walker et al.

[11] Patent Number: 4,932,940
[45] Date of Patent: Jun. 12, 1990

[54] NEEDLE GUARD DEVICE

[76] Inventors: Cedric F. Walker, 2619 Nashville Ave., New Orleans, La. 70118; Juan M. Neito, 1147 Lost Creek Blvd., Austin, Tex. 78746; Bruce A. Broillet, 4830 Salem Villiage Pl., Culver City, Calif.

[21] Appl. No.: 203,287

[22] Filed: Jun. 6, 1988

[51] Int. Cl.⁵ .............................................. A61M 5/00
[52] U.S. Cl. ................................... 604/110; 604/198; 604/263
[58] Field of Search ............... 604/198, 192, 187, 263, 604/136, 110

[56] References Cited

U.S. PATENT DOCUMENTS

| 4,664,654 | 5/1987 | Strauss | 604/198 |
| 4,747,831 | 5/1988 | Kulli | 604/110 |
| 4,752,290 | 6/1988 | Schramm | 604/198 |
| 4,795,432 | 1/1989 | Karczmer | 604/263 X |

FOREIGN PATENT DOCUMENTS

| 1362060 | 4/1964 | France | 604/136 |
| 704152 | 4/1966 | Italy | 604/136 |

Primary Examiner—John D. Yasko
Attorney, Agent, or Firm—Fulwider, Patton, Rieber, Lee & Utecht

[57] ABSTRACT

A needle guard for use with hypodermic syringes and the like to prevent accidental puncturing of the skin of a person who comes in contact with a syringe after it has been used. The invention does not inhibit normal use of the syringe, and positively locks the guard in place after use.

21 Claims, 3 Drawing Sheets

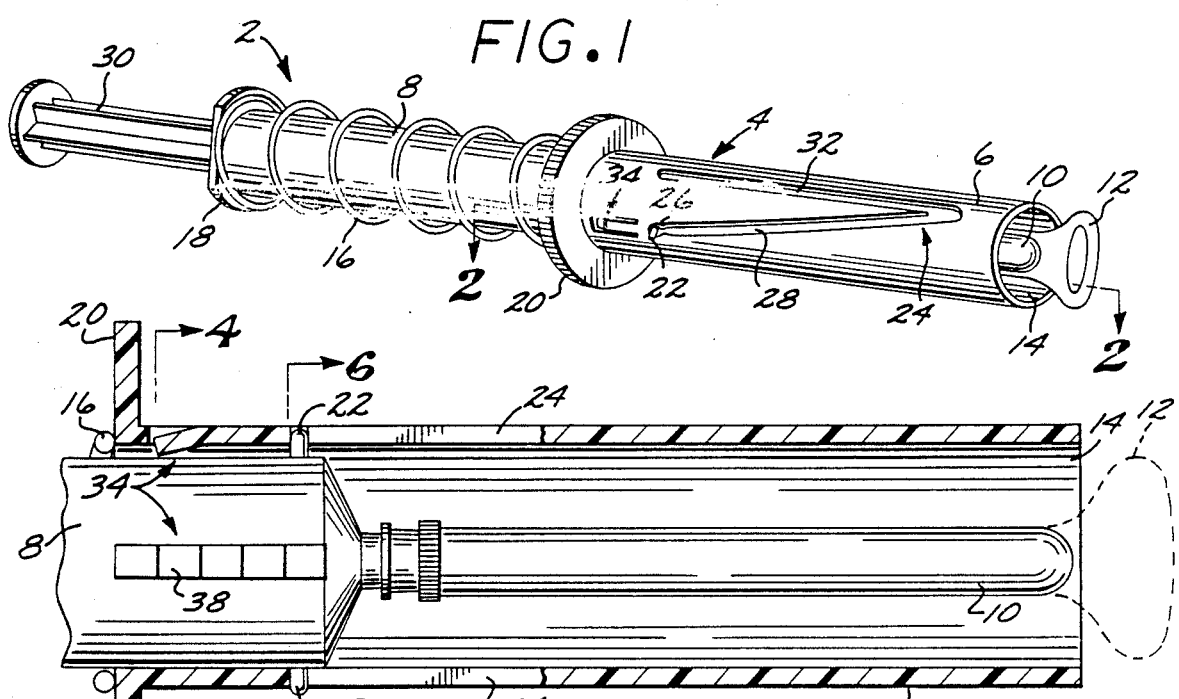

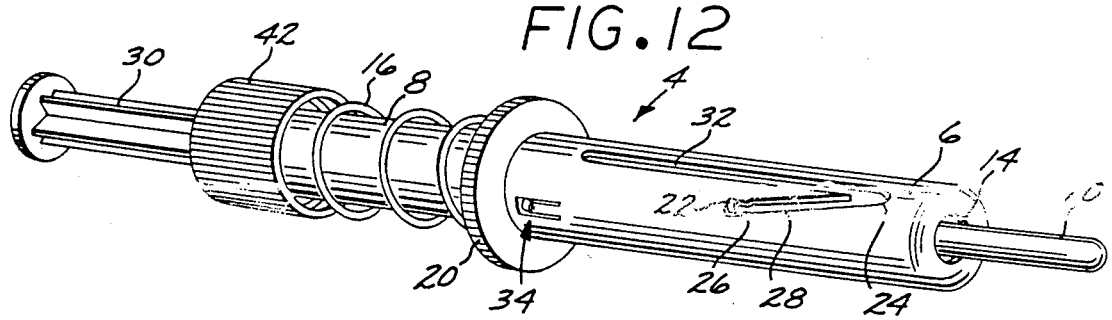
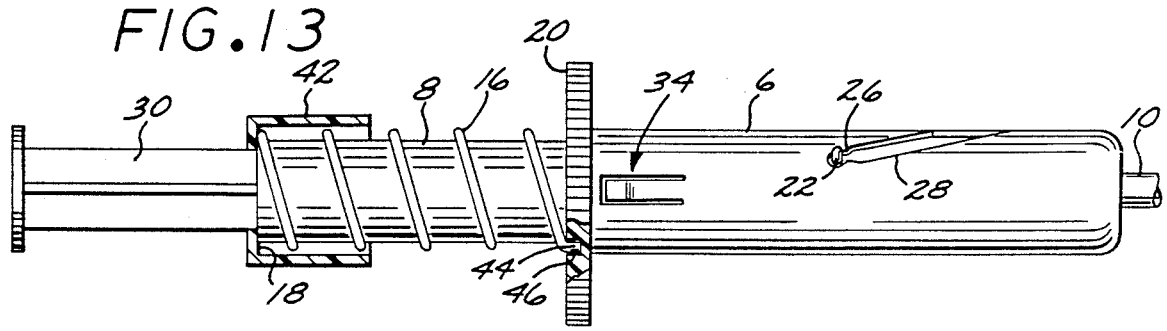
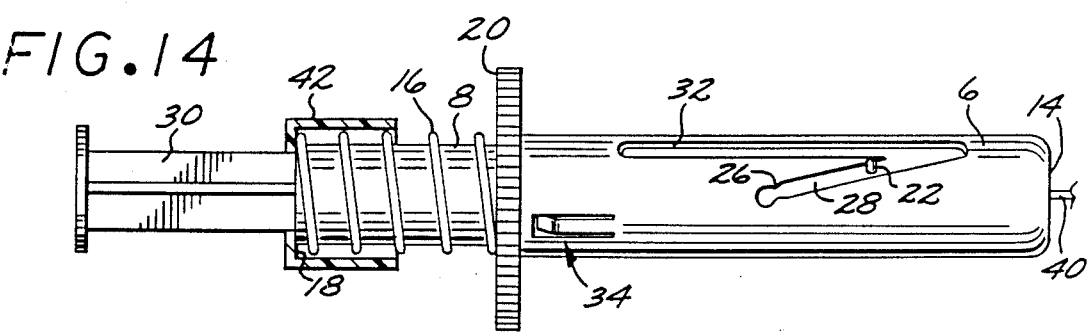
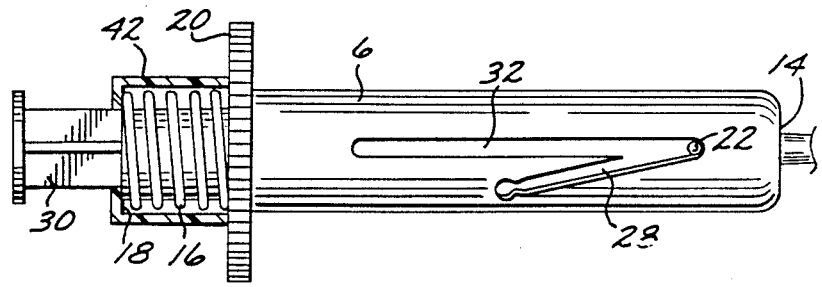
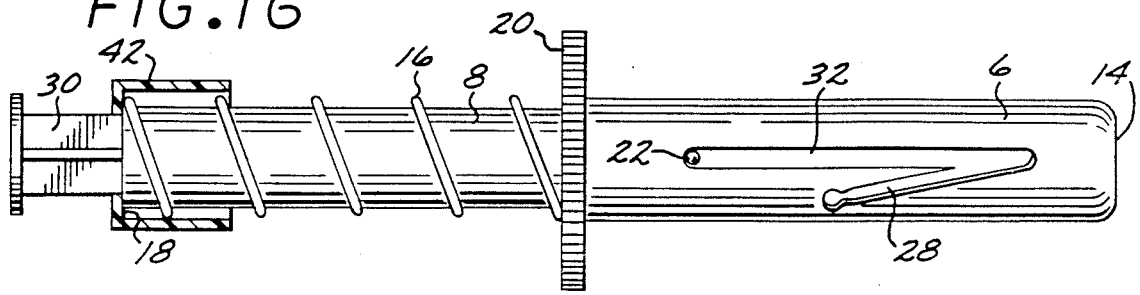

NEEDLE GUARD DEVICE

BACKGROUND

1. Field of The Invention

This invention relates generally to guards used to prevent accidental contact with the tip of a needle or other skin puncturing device used in medicine.

2. Background of the Invention

For many years, considerable effort has been devoted to the production of disposable syringes, catheters, guide wires and other skin piercing instruments used in the diagnosis and care of medical patients. These devices have, for the most part, replaced previous systems that included relatively expensive multiple components used for such purposes and have eliminated the necessity to resterilize such instruments. Due to their disposability, such modern syringes, catheters and other devices have been used extensively in the field for a variety of purposes, including the injection of medicines, the insertion of intravenous devices and the drawing of blood and other fluids for analysis. The very disposability of such devices has resulted in their frequent disposal on the floor or some other convenient location durinq the course of frantic activity associated with an emergency room or other life threatening events. Thus, it is not uncommon for used disposable syringes to be thrown about an emergency room or other critical care area in which time critical medical care is occuring.

This littering of a critical care area, such as an emergency room or intensive care area, with used disposable syringes, with their exposed needles, creates many possible opportunities for health professionals and others in the vicinity to come in contact with such needles. As the technology for producing these needles has improved, they have become thinner and sharper and thus present a very high probability of skin penetration in the event that a part of the human body, whether it is clothed or not, impacts the end of such a needle. While the probability of infection from such needles has always been present to some degree, the infection of a significant portion of the population with the Acquired Immune Deficiency Syndrome (AIDS) virus and the life threatening nature of this disease to anyone infected with it has heightened concern in the medical community about such needle penetration. While the exact mechanism of infection by AIDS is not completely understood, it is well known that the penetration of the skin by a needle contaminated with blood from a person infected with the AIDS virus can cause such an infection.

Since there is often insufficient time during most emergency procedures to screen those being treated for the AIDS virus, there is thus always a possibility that needles used in critical care areas may be contaminated with the AIDS virus. Recent documented cases in which health professionals have been infected by the AIDS virus transmitted through a contaminated needle has heightened this concern and their exists a need to prevent such infections if the quality of emergency care is to be maintained.

The very nature of emergency medical treatment prevents comprehensive use of disposal procedures and the most effective device to accomplish these requirements would be one requiring no manipulation on the part of the operator and one which was relatively simple, inexpensive and moderately foolproof in its operation. Due to the range of procedures which must be undertaken, it would be useful if any such device would be amenable to various types of injections such as intramuscular injections, partial injections, blood drawing and guide wire insertion of catheters. While safety is the most important aspect of any such a use, it would also be helpful if such a safety system were also relatively simple and inexpensive to manufacture.

From the above it may been seen that a serious need exists to protect health care professionals from accidental contact with contaminated needles in an emergency room and other emergency medical treatment environments and that such a safety system should be simple, relatively foolproof and easily operated.

SUMMARY OF THE INVENTION

The present invention provides a means of eliminating accidental contact with a needle that has already been used for a medical procedure, thus reducing the possibility that the needle will accidentally puncture the skin of a person that comes in contact with a used needle. The invention also provides a reliable, efficient and inexpensive way of avoiding accidental puncture of the skin by a used needle of the various types used in medical procedures.

The construction of the present invention is furthermore relatively inexpensive to manufacture, is trouble free in operation and reliable in use and provides the improved security desired without altering the important characteristics of use of syringes and percutaneous needles in normal medical procedures.

In a preferred embodiment, the present invention may be configured in the form of a retractable guard over the needle portion of a medical device used to pierce the skin, such as a syringe or percutaneous needle. The guard is positively biased away from the base of the needle and toward the distal tip by a spring or other suitable elastic means that does not interfere with the normal functioning of the syringe. When the syringe is used, the needle is thrust into the skin while the guard is either withdrawn by the fingers operating at the base of the guard or alternatively, the act of inserting the needle forces the skin surface to push the guard away from the needle. Once the syringe is used and the needle is withdrawn, the spring forces the guard back over the needle, thereby protecting the needle from further accidental penetration of the skin of a person coming in contact with it.

The reliable operation of the guard is effected by a V-shaped notch in the guard in combination with a pin or pins located on the body of a syringe. When the guard is retracted the pin travels down a first leg of the notch until its limit is reached and thereafter retracts up a second leg of the notch after the syringe has been used. The guard is rotated to assure travel of the pin up the second leg of the notch by means of a torsional preload on the spring. By retracting up the second leg of the notch, the pin brings into engagement a locating tab portion of a ratchet on the guard with a mating serration or plurality of serrations on the body of the syringe, thereby preventing a second retraction of the guard after its first use. A slight detent may be placed in the first leg of the V-shaped notch in order to require a certain amount of positive force to begin the retraction of the needle guard. A plurality of configurations of notches may also be used to provide reliable retraction and engagement of the guard after retraction. Internal guide mechanisms may also be used between the syringe and the guard to insure accurate and reliable registration of the guard lock ratchet during and after retraction of the guard.

In another preferred embodiment of the invention, the guard is installed partially retracted with a conventional hand removeable guard over the needle. This configuration is adaptable to the "dart-throwing" techniques used for intramuscular injections, since the needle is partially exposed prior to use. This embodiment is also useful for partial injections and other uses in which the needle must be initially exposed before the guard is actuated. Once the syringe has been used, the guard extends over the full length of the needle as described above.

Other features and advantages of the present invention will become apparent from the following detailed description, taken into conjunction with the accompanying drawings, which illustrate, by way of example, the principals of the invention.

BRIEF DESCRIPTION OF THE DRAWINGS

FIG. 1 is a perspective view of a syringe incorporating a first embodiment of a needle guard according to the present invention.

FIG. 2 is a cross section at 2—2 of FIG. 1, illustrating the internal relationship of the needle quard with the external configuration of a syringe incorporating the invention.

FIG. 3 is a cross section of a needle guard and syringe according to the present invention after the needle guard has been used and has been returned to its locked position.

FIG. 4 is a cross section at 4—4 of FIG. 2 illustrating the relationship of the guard ratchet lock prior to use.

FIG. 5 is a cross section at 4—4 after use, retraction and locking of the needle quard.

FIG. 6 is a cross section at 6—6 of FIG. 2 illustrating the relationship of the guide pins in slots in the needle guard.

FIG. 12 is a perspective view of an alterative preferred embodiment of the invention for a syringe adaptable for techniques used for intramuscular injections.

FIG. 13 is a side view of a syringe incorporating the alternative embodiment prior to use.

FIG. 14 is a side view of a syringe incorporating the alternative embodiment after the injection has been given.

FIG. 15 is a side view of a syringe incorporating the alternative embodiment at the maximum stroke of the plunger.

FIG. 16 is a side view of a syringe incorporating the alternative embodiment after the syringe has been used.

DETAILED DESCRIPTION

Figure 7:
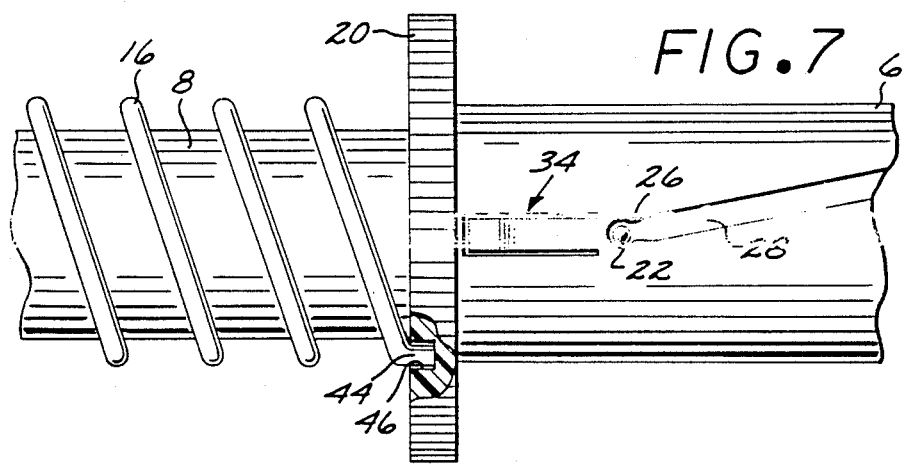
FIG. 7 is an illustration of a needle guard in place on a syringe prior to its use.

While a variety of needle guards have been developed to protect needles prior to and after their use, such guards have generally been of the type that must be manually removed and replaced by the person using the syringe. Although such guards are effective for this use, time and care can not always be to remove and replace such guards in conditions such as medical emergencies occuring in an emergency room or other critical care area, where the full attention of the doctors, nurses and technicians must be directed to rapid care of the patient.

The present invention provides a reliable and efficient means of protecting medical personnel and others prior to and after the use cf such a syringe, thus preventing unnecessary exposure to blood transmitted diseases such as AIDS or other contaminants that might otherwise enter the blood stream if a used needle were contacted.

As illustrated in the exemplary drawings, a first preferred embodiment of the invention includes an essentially tubular needle guard that is held over the needle by a spring acting between a shoulder on the needle guard and a shoulder on the body of the syringe. Pins are mounted on the body of the syringe and protrude through slots located on the needle guard that provide, in combination with a torsional preload in the spring, the means of guiding the needle guard in a predictable manner during its retraction, which occurs when the syringe is used. The pins also serve to prevent the tubular guard from being pushed off of the end of the syringe by the spring. The retraction of the needle guard can either be accomplished by the operator of the syringe pulling the needle guard away with his fingers on the shoulder of the needle guard, or by pushing the syringe downward towards the skin of the patient, thereby retracting the needle guard as the needle pierces the skin. The slot in which the guide pin rides is essentially V-Shaped, with the point of the V located distally, and serves to rotate the needle guard through an angle of approximately 90 degrees during retraction and release to thereby engage a one way ratcheting mechanism with its component parts located on the inside of the needle guard and the outside of the syringe. When the needle guard is released and allowed to move over the needle, rotating the mechanism and engaging the ratchet, the guard thereby prevents another retraction or a further retraction of the needle guard.

A second preferred embodiment is adapted for use in intramuscular injections or other injections that utilize the "dart-throwing" technique, in which the syringe is rapidly flicked by the wrist to quickly and deeply insert the needle. This second preferred embodiment is also adaptable to partial injections and other uses where it is desireable to have the needle partially exposed, with only a conventional guard in place, in the initial configuration prior to the actuation of the guard. This second embodiment is configured with the cylindrical guard partially retracted. Thus, the first leg of the notch is shorter than the second leg and a conventional needle guard is used to prevent contamination of the needle prior to use. When the syringe is used, the operation of the guide is as described above, with suitable changes in the geometry of the slot and ratchet lock to accomodate the different initial stroke.

Thus, it may be seen that the present invention provides a simple, inexpensive and reliable means of preventing the reuse of a needle and also prevents any further contact with the tip of the needle once it has been used, thus substantially enhancing the safety of medical personnel and reducing the probability that they will come in contact with contaminated needles in a hospital environment.

FIG. 1 is a perspective illustration of a needle guard attached to a syringe according to a first embodiment of the present invention. The needle guard, generally designated 4, is an attachment to a conventional syringe 2 that has certain modifications which improve the operation of the needle guard. The tubular guard 6 is sized to retract over the barrel 8 of the syringe 2 when the guard 4 is retracted. A conventional needle protector 10 is removed prior to the time that the syringe is to be used. In practice, it may be advantageous to provide needle protector 10 with an extension 12 which reaches beyond the distal opening 14 and tubular guard 6 in order to assist in removal of the needle protector 10. After the needle protector has been removed, the syringe is used by retracting tubular guard 6 over the body of syringe 8 against the pressure exerted by spring 16 operating against the shoulder 18 of the proximal end of barrel 8, the spring also bearing against the shoulder 20 and tubular guard 6. At least one pin 22 extends through a slot 24 in tubular guard 6. As the guard is retracted, pin 22 is moved past a detent 26 formed as a slight narrowing of the width of the slot before moving down the first leg 28 of the V-Shaped slot 24. Detent 26 is configured to help prevent accidental initial retraction of the needle guard and requires a positive force on the part of the operator to initialize retraction of tubular guard 6. .s the guard is retracted, pin 22 guides the tubular guard 6 through approximately 90 degrees of rotation until the proximal extremity of slot 24 is reached at the end of the first slot 28.

Thereafter, the syringe is used and its contents ejected by depressing plunger 30 to force it through the needle. After the contents have been expelled, pin 22 guides tubular guard 6 to its deployed position by traveling through slot 32 until it reaches its fully deployed position. At that time, a ratchet mechanism, generally designated 34, is engaged to prevent a subsequent withdrawl of the tubular guard 6 from the needle.

From the above description in may be seen that the present invention accomplishes the important functions of preventing inadvertent contact with the needle both before and after its use in a medical procedure and is simple to operate, inexpensive and mechanically simple in its configuration, and has a high reliability of operation under emergency or other stressful medical procedures.

Illustrated in FIG. 2 is a cross sectional view of the guard in its initial position prior to the first retraction. As illustrated, tubular guard 6 in the deployed position has a proximal opening 14 that extends beyond needle guard 10 except for the extension 12. Alternatively, needle protector 10 may be extended to allow easier removal of the needle protector prior to use without initial retraction cf needle guard 4. As the tubular guard 6 is retracted, pins 22 and slots 24 guide tubular guard 6 through ar approximately 90 degree rotation to bring the components of ratchet assembly 34 in registration with one another prior to the release of the guard. Ratchet arm 36 on the body of the needle guard, when retracted, is in registration with ratchet teeth 38 on syringe boyd 8 after the guard is fully retracted and the syringe is empty so that further movement of body 6 in the direction of the deployed position of the guard, assisted by spring 16 acting against shoulder 18, brings the elements of ratchet 34 in registration with one another, thereby preventing any subsequent retraction of the guard. The rotation of guard 6 as pin 22 travels down slot 28 and back up slot 32 is assisted by a torsional preload in spring 16 and appropriate spring indexing devices in shoulders 18 and 20. Initial retraction of the guard is inhibited by detent 26 in slot 28 in combination with pin 22.

FIG. 3 illustrates the arrangement of ratchet mechanism 34 after a needle protector has been removed and the syringe has been used, with the subsequent exposure of needle 40. Tubular guard 6 has now traveled to its deployed position with the proximal opening 14 extending beyond needle 40. Meanwhile, the ratchet arm 36 has come into engagement with ratchet teeth 38 on the syringe body 8 in response to the force exerted by spring 16 against shoulder 20. The resulting ratcheting action prevents subsequent withdrawal of tubular guard 6 after it reaches its deployed position.

FIG. 4 is a cross section at 4—4 of FIG. 2 and illustrates the arrangement of ratchet arm 36 on guard 6 and ratchet teeth 38 on syringe body 8 prior to initial use of the guard. While an angle of 90 degrees is illustrated, those skilled in the art will appreciate that other angles to accomplish the same registration of the ratchet mechanism after use may be used.

FIG. 5 illustrates the arrangement of ratchet arm 36 and ratchet teeth 38 after the use of the syringe, showing that such registration engages the teeth 38 in syringe body 8 with the ratchet arm 36 and tubular guard 6.

FIG. 6 illustrates the arrangement of pins 22 in the first leg 28 of slot 24 formed in tubular guard 6. In this view, the second leg 32 of the slot 24 is illustrated as terminating in a position of 90 degrees to the initial position of slot 28. Pins 22 are mounted in the body 8 of syringe 2, thus providing a positive guide for the travel of the guard as it is retracted and deployed.

FIGS. 7 through 11 illustrate the use of the guard during the typical medical use of a syringe. FIG. 7 illustrates the tubular guard 6 in its initial undeployed position, showing that detent 26 prevents initial movement of tubular guard 6 unless enough force is exerted to overcome both the action of spring 16 against shoulder 20 and the force required to move pin 22 past detent 26 into the first portion of slot 28. Also illustrated is a means of torsionally retaining spring 16 against shoulder 20. In this embodiment spring 16 has a portion 44 that is bent parallel with the axis of the spring and engages a notch 46 in shoulder 20. Spring 16 can be installed with a torsional preload that forces the guard to rotate in the direction of slot 32, thereby assuring that the guard will latch in its safe position after use.

Figure 8:
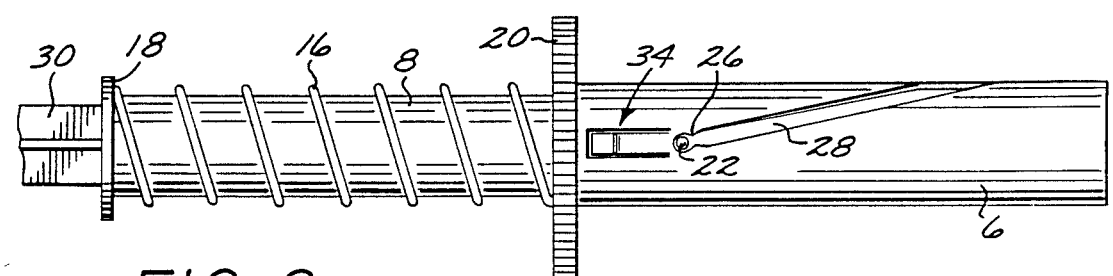
FIG. 8 shows a needle guard at the beginning stage of its retraction.

FIG. 8 further illustrates the arrangement of spring 16 acting against both shoulder 20 on tubular guard 6 and shoulder 18 on syringe 2 prior to either the movement of tubular guard 6 or the depression of plunger 30.

Figure 9:
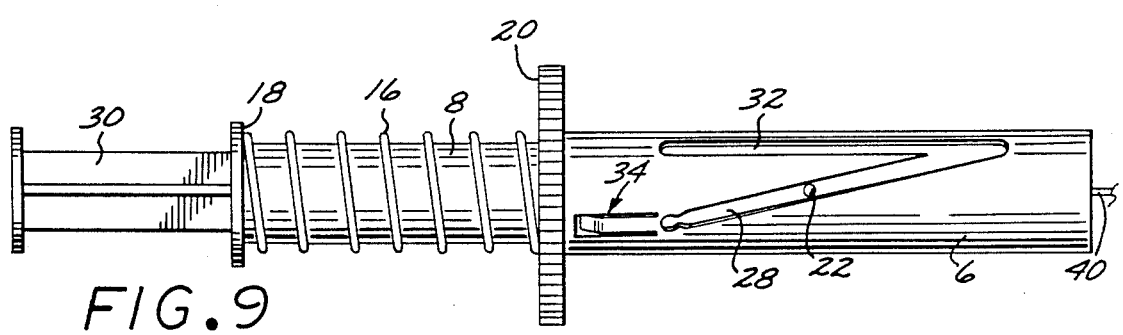
FIG. 9 shows the needle guard partially retracted as a locating pin travels down the first leg of the V-shaped notch.

FIG. 9 illustrates the initial stage of use of the syringe and guard showing that pin 22 has now moved past detent 26 and down the first leg 28 of V-shaped slot 24. Spring 16 has been partially compressed between shoulders 18 and 20 and plunger 30 has been partially depressed, thereby expellinq a portion of the contents of the syringe through needle 40, which is now penetrating the skin cf the patient.

Figure 10:
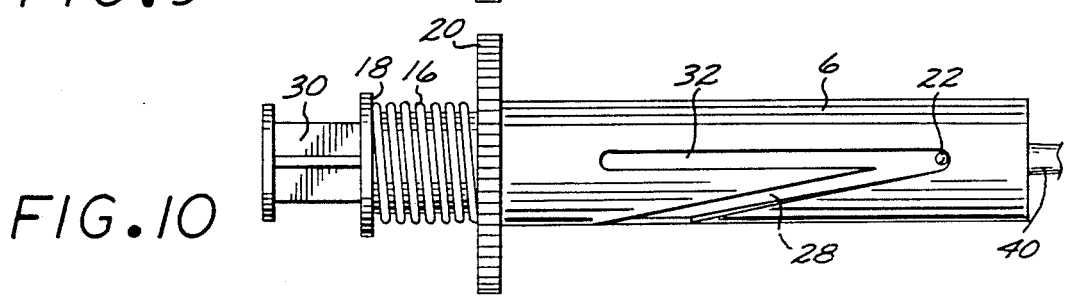
FIG. 10 illustrates the needle guard in its fully retracted position and the syringe fully depressed.

FIG. 10 illustrates a guard and syringe according to the present invention in its fully deployed and fully expelled position. Spring 16 has been fully compressed between shoulders 18 and 20 and the entire contents of the syringe have been expelled due to the full depression of plunger 30. Pin 22 has traveled to the extreme limit of the V-shaped slot 24, and tubular guard 6 is fully retracted. If a guard according to the present invention where not used, this would be the condition of a used syringe not protected with a guard and the full length of the needle would be exposed, thereby substantially increasing the risk that there would be an accidental penetration of the skin of a person coming into contact with a syringe.

Figure 11:
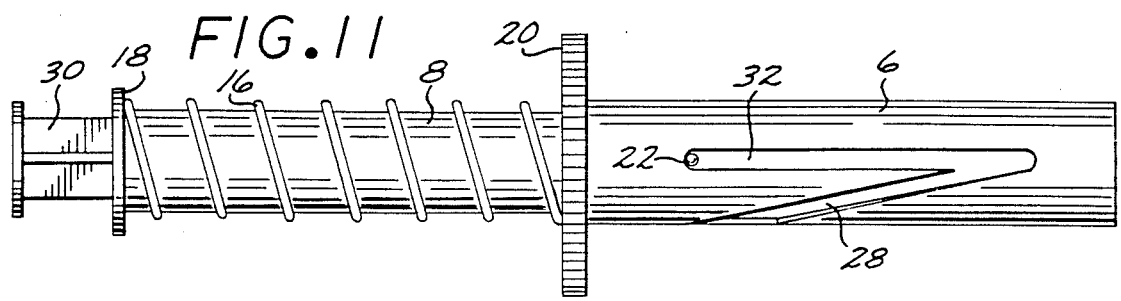
FIG. 11 illustrates the needle guard in its extended position after use.

FIG. 11 illustrates the position after use of the syringe and redeployment of the guard as forced by spring 16 acting between shoulders 18 and 20. Pin 22 has now traveled up the second leg 32 of V-shaped slot 24, thereby engaging the ratchet 34 consisting of ratchet arm 36 and teeth 38. In this position the syringe needle is completely protected by the deployment of the guard and the distal opening 14 of the guard projects a distance beyond the tip of needle 40.

Illustrated in FIG. 12 is a second preferred embodiment of the invention that is adapted to the so-called "dart-throwing" technique for intramuscular injections. This technique utilizes a flip of the wrist to rapidly thrust the needle of a syringe into the skin of a patient. The technique is particularly effective if a dense mass of tissue such as muscle is to be injected. In order to assist this process, it is desireable that there be a portion of the needle initially exposed so that the needle guard does not impede the insertion of the needle and the spring does not cause a rebounding of the needle after insertion. In this embodiment, needle guard 6' is installed so that is is partially retracted, thereby exposing a conventional interior needle guard 10' The first leg 28' of slot 24' is shorter than second leg 32' by the required amount to accomodate the initial retracted portion of the full stroke of the needle guard 6'. A detent 26' is used as described above to prevent movement of the guard prior to depression of the plunger to expeed the contents of the syringe. In this embodiment, a smaller opening 14' in the distal end of guard 6' is shown to illustrate the guard may be configured to prevent the intrusion of even a small finger into the guard after its use. Also illustrated is an alternative configuration of shoulder 18' in which a cylindrical housing 42 is used to both retain the spring 16' and limit the travel of guard 6' thereby placing less stress on pins 22' which would otherwise be used to limit the stroke of the guard. A further important use for shoulder 42 is to prevent the use of a guarded syringe as a conventional syringe by grasping shoulder 42 and pressing plunger 30'. Since the design of shoulder 42 offers no purchase, the user is forced to use shoulder 20' and plunger 30', thereby utilizing the guard 6'. Thus, the configuration of shoulder 42 provides an additional safety feature in forcing the user to engage the guard.

FIG. 13 further illustrates the arrangement of spring 16' acting against both shoulder 20' on tubular guard 6' and shoulder 18' or syringe 2' prior to either the movement of tubular guard 6' or the depression of plunger 30'.

FIG. 14 illustrates the initial stage of use of the syringe and guard showing that pin 22' has now moved past detent 26' and down the first leg 28' of V-shaped slot 24'. Spring 16' has been partially compressed between shoulders 18' and 20' and plunger 30' has been partially depressed, thereby expelling a portion of the contents of the syringe through needle 40', which is now penetrating the skin of the patient.

FIG. 15 illustrates a guard and syringe according to this embodiment of the present invention in its fully deployed and fully expelled position. Spring 16' has been fully compressed between shoulders 18' and 20' and the entire contents of the syringe have been expelled due to the full depression of plunger 30'. Pin 22' has traveled to the extreme limit of the V-shaped stop 24', and tubular guard 6' is fully retracted. If a guard according to the present invention where not used, this would be the condition of a used syringe not protected with a guard and the full length of the needle would be exposed, thereby substantially increasing the risk that there would be an accidental penetration of the skin of a person coming into contact with a syringe.

FIG. 16 illustrates the position after use of the syringe and redeployment of the guard as forced by spring 16' acting between shoulders 18' and 20'. Pin 22' has now traveled up the second leg 32' of V-shaped slot 24', thereby engaging the ratchet 34' consisting of ratchet arm 36' and teeth 38'. In this position the syringe needle is completely protected by the deployment of the guard and the distal opening 14' of the guard projects a distance beyond the tip of needle 40'.

From the above it may be seen that the present invention represents a substantial improvement in the protection of used needles of hypodermic syringes and other skin penetration apparatus which may be used in medical procedures and which may have been contaminated during the course of that use. Furthermore, the invention is easily implemented on otherwise conventional syringe designs and is relatively simple and economical in its use. The invention is particularly advantageous for emergency room and other difficult medical environments since it requires no special procedures or skills on the part of the user.

While a particular form of the invention has been illustrated and described, it will also be apparent to those skilled in the art that various modifications can be made without departing from the spirit and scope of the invention. Accordingly, it is not intended that the invention be limited except as by the appended claims.

We claim:

1. For a needle of the type used in medical procedures, said needle further mounted on a supporting body, a needle guard which comprises:
    an essentially tubular guard member, said guard member sufficiently long enough to fully enclose said needle when said guard member is in a deployed position;
    elastic means to exert a force tending to move said guard member to a deployed position;
    means to guide said guard member from an initial position through a retracted position to a final deployed position;
    means to prevent movement of said guard member beyond said deployed position; and
    ratchet means operative to prevent retraction of said guard member once said guard member reaches said deployed position;
    whereby said retraction of said guard member can only occur once prior to said locking by said ratchet means of said guard member in a final deployed position.

2. The needle guard of claim 1 in which said means to guide said guard member from an initial position through a retracted position to a deployed position further comprises a guide slot in said guard and a retaining member attached to said body.

3. The needle guard of claim 1 in which said guide slot further comprises an essentially V-shaped slot with the apex of said V-shaped slot located towards the distal end of said guard.

4. The needle guard of claim 3 wherein said means to prevent movement of said distal end of said guard beyond said deployed position further comprises said guide slot and said retaining member.

5. The needle guard of claim 2 wherein said retaining member further comprises a pin attached to said body and extending radially therefrom through said slot.

6. The needle guard of claim 1 wherein said ratchet means further comprises a ratchet member located on the exterior of said body and a ratchet member located on the interior of said guard which are brought into registration with one another when said guard is moved to its deployed position.

7. The needle guard of claim 1 in which said guard member further comprises a narrowing of the distal end of said guard member to thereby substantially prevent access to said needle when said guard member is in said deployed position.

8. The needle guard of claim 1 wherein said elastic means further comprises a spring extending between a shoulder on said guard member and a shoulder on said body.

9. The needle guard of claim 8 wherein said elastic means further comprises means to anchor the ends of said spring against said guard member and said body to thereby provide resistance to relative torsional movement between said guard member and said body.

10. The needle guard of claim 2 wherein said guide slot further comprises means to inhibit movement from said initial position until a predetermined amount of force is applied.

11. A needle guard guard for hypodermic syringes of the type including a body enclosing a cylindrical cavity, a needle attached to said body and connected to said cavity and a plunger which comprises:
a shoulder near the proximal end of said syringe body;
at least one first ratchet element located on said body near the distal end of said body;
an essentially cylindrical needle guard, said guard including an opening at its distal end and a shoulder at its proximal end;
a guide slot in the body of said guard, said guide slot including portions of said slot arranged at an angle to one another, said portions of said slot meeting near the distal end of said guard and separated at their other ends;
a second ratchet element on the inside of said guard near the proximal end thereof;
pins mounted on said body and extending through said slots to locate said needle guard relative to said body; and
a spring extending between said shoulder on said syringe and said shoulder on said guard, said spring exerting a force in the direction of the deployed position of said guard;
whereby retraction of said guard from its initial deployed position is guided by said pins in said slots until retraction is complete, said pins thereafter traveling in said second portion of said slot until said deployment is complete and said ratchet elements are engaged, thereby preventing a second retraction of said guard from said second deployed position.

12. The needle guard assembles of claim 11 wherein said elastic means further comprises means to anchor the ends of said spring against said body and said guard to thereby provide resistance to relative torsional movement between said body and said guard.

13. The needle guard assembly of claim 11 wherein said guide slot further comprises means to inhibit movement from said initial position until a predetermined amount of force is applied to said guard.

14. A needle guard assembly which comprises:
a supporting body attached to said needle;
an essentially cylindrical guard for said needle;
means to slidably locate said guard relative to said needle;
elastic means operative to urge said guard to a deployed position covering said needle;
latching means operative to latch said guard in a deployed position covering said needle; and
guide means including a pair of guide slots in said guard forming an acute angle operative to guide said guard from an initial position to a deployed position covering said needle.

15. The needle guard assembly of claim 14 in which said guide means to guide said guard from an initial position to a deployed position further comprises a retaining member attached to said body.

16. The needle guard assembly of claim 14 wherein said means to slidably locate said guard relative to said needle further comprises means to prevent movement of said distal end of said guard beyond said deployed position.

17. The needle guard assembly of claim 15 wherein said retaining member further comprises a pin attached to said body and extending radially therefrom through said pair of guide slots.

18. The needle guard assembly of claim 14 wherein said elastic means further comprises a spring extending between a shoulder on said guard and a shoulder on said body, and means to anchor the ends of said spring against said guard and said body to thereby provide resistance to relative torsional movement between said guard and said body.

19. The needle guard assembly of claim 14 wherein said initial position of said guard exposes at least a portion of said needle.

20. A needle guard assembly which comprises:
a supporting body attached to said needle;
an essentially cylindrical guard for said needle;
means to slidably locate said guard relative to said needle;
elastic means operative to urge said guard to a deployed position covering said needle;
latching means operative to latch said guard in a deployed position covering said needle; and
guide means operative to guide said guard from an initial position to a deployed position covering said needle, comprising a guide slot in said guard and a retaining member attached to said body, said guide slot having an essentially V-shaped slot with the apex of said V-shaped slot located toward the distal end of said guard.

21. A needle guard assembly which comprises:
a supporting body attached to said needle;
an essentially cylindrical guard for said needle;
means to slidably locate said guard relative to said needle;
elastic means operative to urge said guard to a deployed position covering said needle;
latching means operative to latch said guard in a deployed position covering said needle, said latching means including a ratchet member located on the exterior of said body and a ratchet member located on the interior of said guard which are brought into registration with one another when said guard is guided to its deployed position; and
guide means operative to guide said guard from an initial position to a deployed position covering said needle.

* * * * *

UNITED STATES PATENT AND TRADEMARK OFFICE
CERTIFICATE OF CORRECTION

PATENT NO. : 4,932,940

DATED : June 12, 1990

INVENTOR(S) : Cedric F. Walker, Juan M. Nieto and Bruce A. Broillet

It is certified that error appears in the above-identified patent and that said Letters Patent is hereby corrected as shown below:

Title page:

Cedric F. Walker's zip code should read 70115 not 70118.

Juan M. Nieto's last name is spelled incorrectly. It is spelled Nieto, not Neito.

Signed and Sealed this

Twenty-ninth Day of October, 1991

*Attest:*

HARRY F. MANBECK, JR.

*Attesting Officer*      *Commissioner of Patents and Trademarks*